United States Patent [19]
Shimizu

[11] Patent Number: 5,738,681
[45] Date of Patent: Apr. 14, 1998

[54] LASER MEDICAL TREATMENT APPARATUS

[75] Inventor: Susumu Shimizu, Kodaira, Japan

[73] Assignee: Kabushiki Kaisha Toshiba, Kawasaki, Japan

[21] Appl. No.: 649,321

[22] Filed: May 17, 1996

Related U.S. Application Data

[62] Division of Ser. No. 217,568, Mar. 25, 1994, Pat. No. 5,554,156.

[30] Foreign Application Priority Data

Mar. 26, 1993 [JP] Japan .................. 5-68701

[51] Int. Cl.⁶ .................. A61B 17/36
[52] U.S. Cl. .................. 606/17; 606/9
[58] Field of Search .................. 606/9, 10, 11, 606/12, 15, 16, 17; 433/29, 215, 216; 372/58, 59, 60, 76

[56] References Cited

U.S. PATENT DOCUMENTS

| | | | |
|---|---|---|---|
| 4,706,257 | 11/1987 | Brunet et al. | 372/59 X |
| 4,732,448 | 3/1988 | Goldenberg et al. | 606/17 X |
| 4,917,083 | 4/1990 | Harrington et al. | 606/15 |
| 4,928,286 | 5/1990 | Foreman et al. | 372/58 X |
| 5,020,995 | 6/1991 | Levy | 606/15 X |
| 5,166,947 | 11/1992 | Duncan | 372/59 X |
| 5,344,418 | 9/1994 | Ghaffari | 606/9 |
| 5,388,987 | 2/1995 | Badoz et al. | 606/18 X |
| 5,388,988 | 2/1995 | Goisser et al. | 606/17 X |
| 5,496,309 | 3/1996 | Saadat et al. | 606/15 |
| 5,558,670 | 9/1996 | Konwitz et al. | 606/18 |

*Primary Examiner*—Jennifer Bahr
*Assistant Examiner*—Sonya Harris-Ogugua
*Attorney, Agent, or Firm*—Oblon, Spivak, McClelland, Maier & Neustadt, P.C.

[57] ABSTRACT

A laser apparatus for medical treatment use in which a laser beam is irradiated on a portion of a human body to be treated comprises a laser beam generation unit for generating a laser beam of giant pulse, a laser beam guide member having one end through which the laser beam from the laser beam generation unit is guided, and a hand piece attached to another end of the laser beam guide member and irradiating the laser beam to the portion to be treated. A beam converging point is formed within a laser beam propagating path formed in at least one of the light guiding means and the hand piece and a stay of air is prevented from a predetermined region in the laser beam propagating path including at least the beam converging point at which the air stays. The predetermined region is positioned within the hand piece or the laser beam guide member. The air stay is prevented by means of producing a vacuum state, gas seal state or air flow state in the predetermined region.

12 Claims, 6 Drawing Sheets ic treatment apparatus hereinafter, employed in such treatment of birthmarks. In the hand piece shown in FIG. 11, a laser beam LB delivered from a laser generator, for example by way of a mirror joint, is focused by means of a first lens 100 and it is then incident upon a uniform light irradiation member (known commercially as "KALEIDOSCOPE", Trade Name of Toshiba Corporation) 101 which has an axially extended cavity having a predetermined diameter. By means of this uniform light irradiation member 101, the laser beam of a circular Gaussian distribution is converted to have an angular uniform output distribution. This uniform output beam is further irradiated on a skin surface to be subjected to the medical treatment through a second lens 102. On the other hand, the hand piece shown in FIG. 12 is the one with more emphasis on its simplicity of construction than uniform light irradiation of FIG. 11, and the laser beam LB is focused by simply using a lens 103. The area of irradiation is varied by adjusting the distance from the lens 103. Both of these hand pieces use a beam spreading portion after the light converging point F of the laser beam and are constructed to have the uniform light irradiation member or to adjust the location of treatment, i.e. portion of a skin surface to be treated.

LASER MEDICAL TREATMENT APPARATUS

This is a Division of application Ser. No. 08/217,568 filed on Mar. 25, 1994, U.S. Pat. No. 5,554,156.

BACKGROUND OF THE INVENTION

1. Field of the Invention

The present invention relates to a laser apparatus for medical treatment use particularly for treating a birthmark or the like and, more particularly, relates to a laser medical treatment apparatus in which a giant pulse that is most effective for the treatment of a deep birthmark is outputted by using such techniques as the Q-switching method.

2. Description of the Related Art

Medical treatment of birthmarks by utilizing laser beams are effected by destroying an abnormal tissue such as melanophore in a skin of a human body, for example, which causes the birthmark. The principle of this treatment is that, by irradiating a laser beam having a wavelength which will not be well absorbed by normal tissues but will be absorbed at a higher rate by the abnormal tissue, the abnormal tissue may be destroyed while holding damage to the normal tissues to a minimum.

FIGS. 11 and 12 show conventional examples of a hand piece of a laser apparatus for medical treatment use, called laser medical treatment apparatus hereinafter, employed in such treatment of birthmarks. In the hand piece shown in FIG. 11, a laser beam LB delivered from a laser generator, for example by way of a mirror joint, is focused by means of a first lens 100 and it is then incident upon a uniform light irradiation member (known commercially as "KALEIDOSCOPE", Trade Name of Toshiba Corporation) 101 which has an axially extended cavity having a predetermined diameter. By means of this uniform light irradiation member 101, the laser beam of a circular Gaussian distribution is converted to have an angular uniform output distribution. This uniform output beam is further irradiated on a skin surface to be subjected to the medical treatment through a second lens 102. On the other hand, the hand piece shown in FIG. 12 is the one with more emphasis on its simplicity of construction than uniform light irradiation of FIG. 11, and the laser beam LB is focused by simply using a lens 103. The area of irradiation is varied by adjusting the distance from the lens 103. Both of these hand pieces use a beam spreading portion after the light converging point F of the laser beam and are constructed to have the uniform light irradiation member or to adjust the location of treatment, i.e. portion of a skin surface to be treated.

If, however, the above described conventional hand pieces are applied to a laser medical treatment apparatus which outputs a giant pulse by means of such techniques as the Q-switching method, the peak power of laser reaches a very high value such as several tens of MW or more. An air breakdown or the so-called laser discharge occurs at the converging position (focus) F of the laser beam and in the vicinity thereof so as to absorb the laser energy. Thus, there has been a problem that the energy at the treatment skin surface is significantly reduced. In other words, since an energy necessary for the aimed treatment is not obtained, the treatment of a deep birthmark is difficult because the laser beam cannot penetrate deeply inside the skin.

On the other hand, it is supposedly possible with a lens-type hand piece (structure shown in FIG. 12) to use the lens 103 having a relatively large focal length so that the treatment surface may be set on the lens side of the beam converging point F in order to avoid a laser discharge. However, in this method, if the laser is erroneously emitted into the air, the laser beam is converged (up to the beam converging point F) as it travels farther from the specified treatment surface. Since the energy density thereof becomes larger, a problem in safety operation will be raised even if protective glasses are worn.

SUMMARY OF THE INVENTION

An object of the present invention is to substantially eliminate defects or drawbacks encountered in the prior art described above and to provide a laser medical treatment apparatus in which, even though the laser beam is converged in the course of the beam path to the treatment surface, a laser discharge at such converging point can avoided or controlled so that a laser energy necessary for the treatment is secured.

It is another object of the present invention to provide laser medical treatment apparatus in which a laser discharge, that is likely to occur in the apparatus capable of outputting a giant pulse, can be avoided or controlled so that a deep birthmark can be effectively treated.

It is a further object of the present invention to provide a laser medical treatment apparatus having a structure capable of eliminating unreasonable setting of the treatment surface between the lens and the light converging point in order to avoid a laser discharge.

It is a still further object of the present invention is to provide a laser medical treatment apparatus capable of obtaining a uniform laser beam energy density at the portion to be treated.

These and other objects can be achieved according to the present invention by providing a laser apparatus for medical treatment use in which a laser beam is irradiated on a portion of a human body to be treated comprising:

a laser beam generation means for generating a laser beam of giant pulse;

a guide means having one end through which the laser beam outputted from the laser beam generation means is guided;

a hand piece attached to another end of the light guiding means and irradiating the laser beam to the portion to be treated;

means for forming a beam converging point within a laser beam propagating path formed in at least one of the light guiding means and the hand piece; and means for preventing a stay of air from a predetermined region in the laser beam propagating path including at least the beam converging point at which the air stays.

In a preferred embodiment, the predetermined region is positioned within the hand piece. In this embodiment, the air stay preventing means is connected to the hand piece and comprises a means communicated with the predetermined region and adapted to produce a vacuum state, a gas sealing state or air flow state in the predetermined region. The means for forming the beam converging point comprises a light guiding lens disposed in the hand piece for narrowing the laser beam having been guided by the light guiding means to form the beam converging point, and a uniform light irradiation member (for example, commercially known as KALEIDSCOPE of Toshiba Corporation) disposed toward the portion to be treated from the beam converging point and receiving a transmitting beam of the light guiding lens to output a uniformed laser beam. The light guiding means comprises a mirror joint assembly.

In another embodiment, the predetermined region is positioned within the light guiding means. In this embodiment, the air stay preventing means is connected to the light guiding means and comprises a means communicated with the predetermined region and adapted to produce a vacuum state, a gas sealing state or air flow state in the predetermined region. The light guiding means comprises a cylindrical body having one end through which the laser beam is guided therein and another end connected to the hand piece, a light guiding lens for narrowing the laser beam having been guided from the laser beam generation means and an optical fiber means disposed in the cylindrical body on a downstream side of the light guiding lens, the optical fiber means comprising an outer clad coaxially disposed in the cylindrical body and a number of optical fibers disposed in the clad and extending from an input side facing the light guiding lens to an output side facing the hand piece.

A modified embodiment further comprises a uniform light irradiation means disposed in the cylindrical body between the light guiding lens and the optical fiber means, the uniform light irradiation means has an input side end positioned downstream side of the beam converging point and an output side end connected to the input side end of the optical fiber means.

In the laser medical treatment apparatus according to the present invention, a laser beam of giant pulse outputted by the laser generation means such as a ruby laser reaches the hand piece as guided by such light guiding means as a mirror joint and is irradiated on the treatment surface from the hand piece. In order to make uniform the beam irradiation output, the laser beam is converged in the course of propagation of the laser beam, for example within the hand piece, so as to form a beam converging point. Here, since the space of a predetermined region including such beam converging point is, for example, in a vacuum state, in a state with such gases as Ne, H being sealed therein or in a state where air continually flows in and out, the threshold value of laser discharge is considerably higher comparing with the case where air is simply caused to stay therein. For this reason, laser discharge at the beam converging point is prevented or controlled so that the beam energy is hardly vanished. An expected sufficient beam energy may thus be obtained at the treatment surface, which is suitable in the treatment of a deep birthmark.

A similar effect may be obtained in the case where the beam converging point is not specifically formed in the hand piece but is formed within the mirror joint. Further, even if the hand piece is of a lens type having only a single projecting lens mounted thereon, laser discharge at the beam converging point may be securely prevented and/or controlled.

Furthermore, according to the present invention, the mirror joint assembly is substituted with a cylindrical light guide means in which the optical fiber means composed of a number of fine optical fibers is disposed to increase the light energy density. In this embodiment, the laser beam irradiation means may be further disposed in connection with the optical fiber means to make uniform the energy distribution at the laser beam output side end of the optical fiber means. The use of the optical fiber means may be eliminate the use of mirror joint assembly.

The natures and further features of the present invention will be made more clear from the following description with reference to the accompanying drawings.

DESCRIPTION OF THE PREFERRED EMBODIMENTS

A first embodiment of the present invention will be described hereunder with reference to FIGS. 1 to 3.

Figure 1:
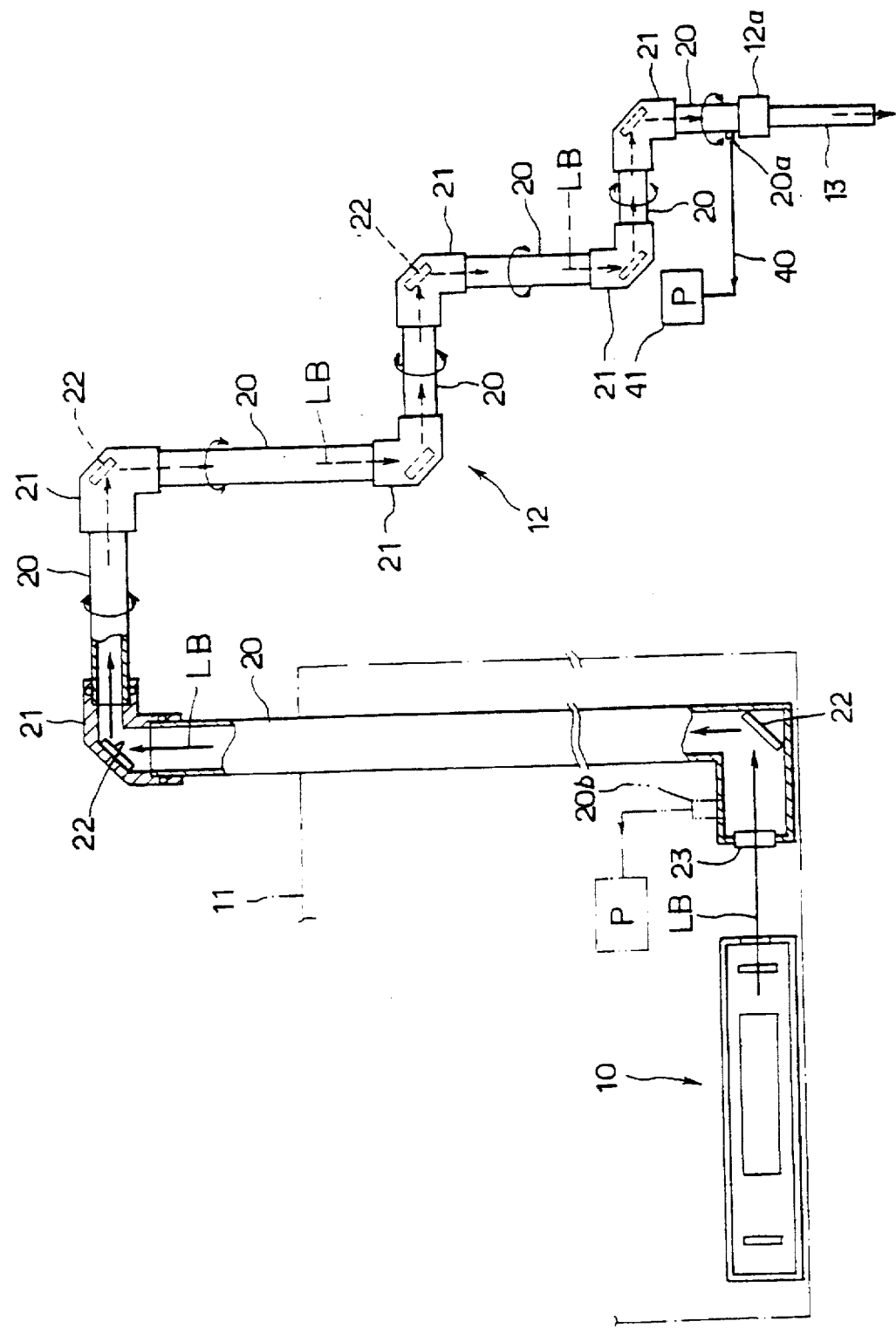
FIG. 1 shows an example of an entire structure of a laser medical treatment apparatus according to one embodiment of the present invention.

FIG. 1 shows a laser apparatus for medical treatment use, called laser medical treatment apparatus hereinafter, for treating a birthmark or the like of a human body. The laser medical treatment apparatus includes an apparatus body 11 incorporating a ruby laser 10 as a laser beam generation means, a mirror joint assembly 12 serving as a light guiding means optically coupled to the ruby laser 10, and a hand piece 13 coupled to the terminal end of the mirror joint assembly 12 through a joint 12a. A portion of a rising portion of the mirror joint assembly 12 is disposed within the apparatus body 11.

The ruby laser 10 uses a solid ruby as a laser medium and is capable of providing an output by converting by means of a Q-switch an energy energized by a power supply device, not shown, into a laser output having a large peak power (giant pulse) with a narrow pulse width. Since the laser beam of such giant pulse is capable of penetrating deeply from the skin surface, it is suitable in treating a deep birthmark or the like. The laser beam outputted from an output portion such as output mirror of the ruby laser 10 is irradiated on an input surface of the mirror joint assembly 12 at the next stage.

The mirror joint assembly 12 has a cylindrical body in a plurally articulated manner, for example, seven joints in the illustrated embodiment, in which a plurality of slender cylindrical bodies 20, - - -, 20 (cylinders) serving as the arm are connected as indicated in FIG. 1 by a plurality of joints 21, - - -, 21. The joints 21, - - -, 21 are each formed into an L-shape as shown in FIG. 1, and each of the cylindrical bodies 20, - - -, 20 is connected to both ends of each joint 21 in a rotatable manner in the direction of an arrow with respect to the joint 21. Disposed at the interior of the joints 21, - - -, 21 are respective mirrors 22, - - -, 22 for perpendicularly bending the laser beam path. A light transmitting member 23 is disposed at the input surface of the mirror joint assembly 12. A light converging point of laser beam (beam converging point: focus) may be formed, as required by the design specification of the beam propagating path, between the light transmitting member 23 and a first mirror 22 for upward reflection. The interior of the mirror joint assembly 12 is formed to provide an air-tight condition by using an O-ring or the like at each coupling portion.

Figure 2:
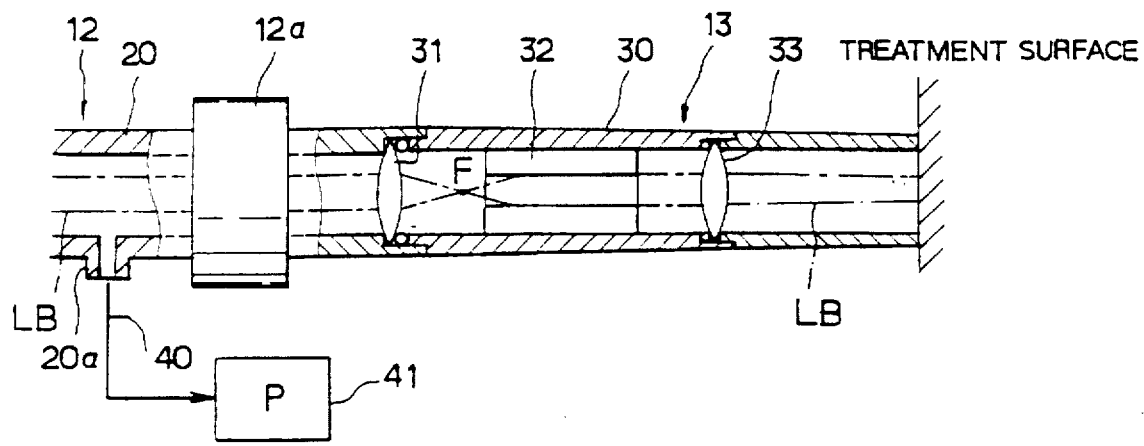
FIG. 2 is an axial sectional view of the hand piece of the apparatus of FIG. 1.

As shown in FIG. 2, the hand piece 13 has a cylindrical body (cylinder) 30 which is to be grasped by an operator. A light guiding lens 31, a uniform light irradiation member 32 in the form of a prism-shaped cavity, such as KALEIDSCOPE (Trade Name of Toshiba Corporation) commercially known, and a projecting lens 33 are disposed at the interior of the cylinder 30 in order from the side of the mirror joint assembly 12 with respective predetermined intervals. Further, a vacuuming port 20a is formed at a position on the cylinder 30 toward the mirror joint assembly 12 from the light guiding lens 31, the vacuuming port 20a being connected to a vacuum pump 41 through a hose 40. The hose 40 is extended to trail the outer surface of the mirror joint assembly 12.

Figure 3:
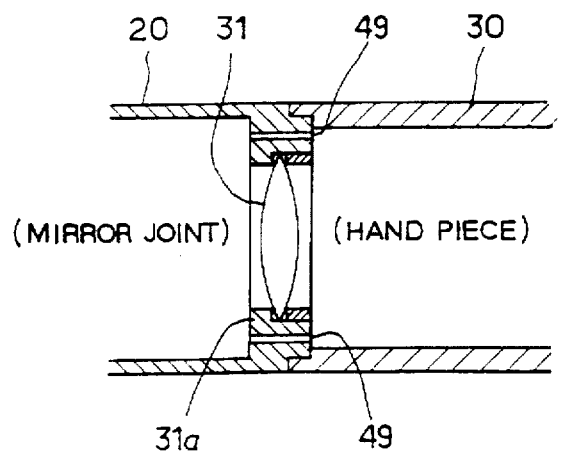
FIG. 3 is a partial sectional view for explaining air holes between a hand piece and a mirror joint assembly of the apparatus of FIG. 1.

As shown in FIG. 3, the light guiding lens 31 is supported at the interior of the cylinder 30 by a ring-like supporting member 31a in such a manner as to separately arrange the mirror joint side and the hand piece side into different chambers and air holes 49, - - -, 49 for communicating such two separated chambers with each other are formed on the support member 31a. On the other hand, the projecting lens 33 is attached by means of an O-ring or the like as shown in FIG. 2 so as to provide an air-tight condition between the uniform light irradiation member side and the irradiation surface, i.e. treatment skin surface, side. According to the above structure, the interior space, formed as a beam propagating path, from the mirror joint assembly 12 to the projecting lens 33 of the hand piece 30 is in communication throughout so as to be kept in an air-tight condition from the outside.

The operation of this embodiment will be described hereunder.

In the laser medical treatment apparatus of this embodiment, the vacuum pump 41 is operated at least before the medical treatment. Air in the beam propagating path from the mirror joint assembly 12 to the projecting lens 33 of the hand piece 13 is thereby gradually exhausted to increase the degree of vacuum thereof. After the degree of vacuum reaches a predetermined value, the medical treatment is started. During such treatment, a cock, not shown, of the vacuuming port 31a may be closed to seal off the beam propagating path in a vacuum condition, or alternatively, the operation of the vacuum pump 41 may be continued with the cock being opened. In either case, the degree of vacuum of the set value or higher is secured in starting the laser medical treatment in the space of the laser propagating path from the mirror joint assembly 12 to the hand piece 13.

In such vacuum state, a laser beam LB of giant pulse outputted from the ruby laser 10 is guided by the mirror joint assembly 12 to reach the hand piece 13 which is grasped by the operator. The hand piece 13 is suitably extended to the location of the birthmark to be treated by the rotation of each of the joint portions of the mirror joint assembly 12 and the beam output surface at the terminal end thereof is pressed against the treatment surface.

In the hand piece 13, the inputted laser beam LB is narrowed by the light guiding lens 31 to form a beam converging point F at a predetermined position in the beam propagating path between the light guiding lens 31 and the uniform light irradiation member 32. In this embodiment, since, as described, the propagating path as a whole including the beam converging point F is in its state of a vacuum higher in degree than a set value, the discharge threshold value thereof is significantly higher than a case where air exists as a medium. For this reason, laser discharge at the beam converging point F which has conventionally occurred when using a giant pulse is prevented or controlled.

The laser beam LB having a predetermined beam diameter is then incident on the cavity portion of the uniform light irradiation member 32. Upon repeating several times of total reflection, the laser beam LB which has entered the uniform light irradiation member 32 is converted from a beam of a circular Gaussian distribution into an angular-shaped beam of uniform output distribution. Since the uniform light irradiation member 32 effects uniforming of the beam at its cavity portion, it can attain such function as uniforming the output without causing a damage by the laser even if a giant pulse is used. The output beam of the uniform light irradiation member 32 becomes a beam having an angular cross section of a predetermined size as transmitted through the projecting lens 33 and is projected on the treatment surface. The laser medical treatment of a deep birthmark or the like can be thus effected.

Since, in this embodiment, laser discharge at the beam converging point F occurs with little likelihood, the beam energy reaching the treatment surface is hardly reduced so that a predetermined energy necessary for the treatment is ensured and the treating energy is stable. As a result, such a disadvantage encountered in the prior art as that the treatment is insufficient due to lack of energy can be eliminated and a deep birthmark or the like can be well treated by means of a giant pulse.

It should be noted that, in the case of a design where a beam converging point F is formed between the light transmitting member 23 and the first mirror 22 for upward reflection at the incident side of the mirror joint assembly 12, the laser discharge at such light converging point F can also be surely prevented or controlled at the same time in a secure manner. The above described effect of preventing a reduction in the treatment energy thus becomes even more conspicuous.

Furthermore, since, in this embodiment, the cavity portion of the uniform light irradiation member 32 is evacuated, too, there is an advantage that the optical characteristic of the reflecting surface in the cavity thereof is further improved. Further, although the giant pulse may be guided by means of an optical fiber, it may be suitably guided in this embodiment by the mirror joint assembly 12 in comparison with a case of single optical fiber. Since, at this time, the interior of the mirror joint assembly 12 is also kept in its state of vacuum, there is also an advantage that the optical characteristic of the mirror surface is stabilized.

It should be further noted that the vacuuming port for producing a vacuum condition is not limited to the one as described, and it is also possible for example to form it between the light transmitting member 23 of the mirror joint assembly 12 and the first mirror 22 for the upward reflection as indicated by an imaginary line 20b in FIG. 1. In this manner, a hose reaching the vacuum pump may be incorporated into the body of the apparatus to prevent the hose from being externally dragged around. Further, in the case of the construction where the whole of the beam propagating path associated with the laser generator (ruby laser) 10, the mirror joint assembly 12 and the hand piece 13 are kept in an air-tight condition in an integrated manner, the vacuuming port may be formed on the laser generator 10. Therefore, in addition to facilitating the dragging operation of the hose as described, the characteristic of the optical components on the beam path can be stabilized, being advantageous.

Other embodiments according to the present invention will now be described with reference to FIGS. 4 to 8, and it should be noted that identical or like members as the components of the above described embodiment are denoted by like reference numerals and description thereof will be omitted or be made in brief.

Figure 4:
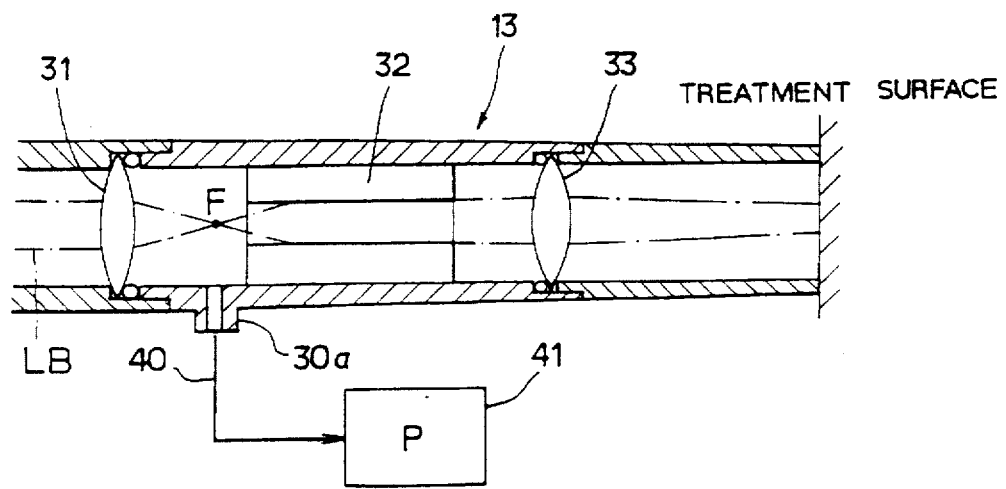
FIG. 4 is an axial sectional view of the hand piece according to a first example of another embodiment.

First, FIG. 4 shows one example of construction of the hand piece 13 according to a first example of other embodiments of the present invention. This hand piece 13 is constructed so that only the interior of the hand piece is to be kept in the state of a vacuum. Specifically, both the light guiding lens 31 and the projecting lens 33 are held in an air-tight manner with respect to the cylinder 30. Here, a vacuuming port 30a is formed between the light guiding lens 31 and the uniform light irradiation member 32 of the cylinder 30 so that the internal air is vacuumed by a vacuum pump 41 through the port 30a.

In this manner, a laser discharge will be surely prevented or controlled at the beam converging point F between the light guiding lens 31 and the uniform light irradiation member 32 so as to obtain effects and advantages similar to those described for the former embodiment.

Further, it should be noted that, in this first example, only the interior of the hand piece 13 is brought into its state of vacuum. Therefore, by designing the hand piece 13 such that it is attached detachably to the mirror joint assembly 12, and the hand piece 13 which has been sealed off into its state of vacuum at another location can be brought to the location of treatment to attach it to the mirror joint assembly 12 for use. Thus, by providing a detachable hand piece 13 in this manner, a hose is not hung from the mirror joint 12 during the treatment whereby the operability for the treatment can be greatly improved.

Figure 5:
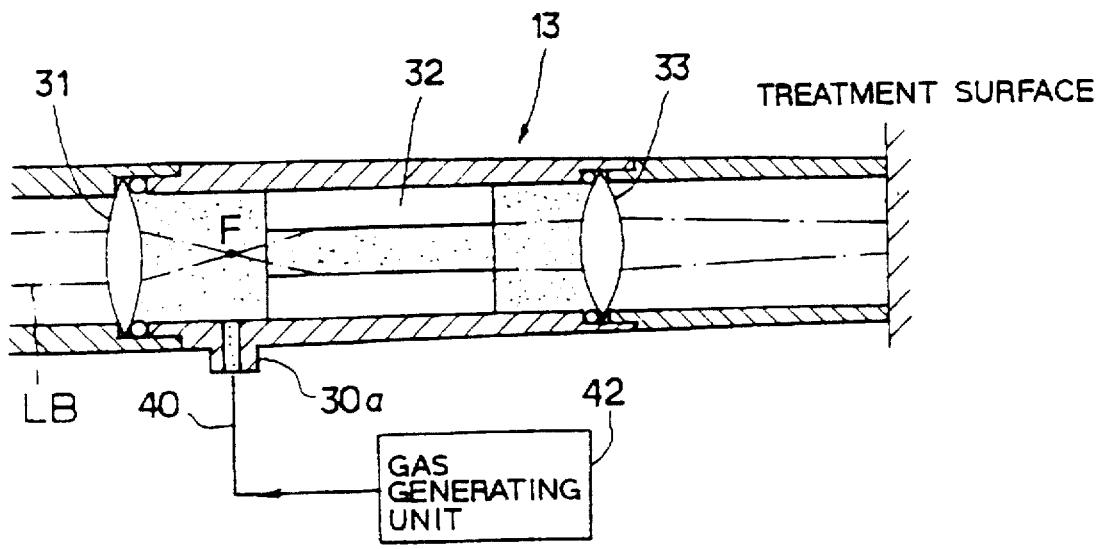
FIG. 5 is an axial sectional view of the hand piece according to a second example.

Next, FIG. 5 shows another construction of the hand piece 13 according to a second example. While the hand piece 13 shown in FIG. 5 is of the same construction as the hand piece of FIG. 4, a gas generating unit 42 such as of He, N, etc., is connected to the port 30a through a hose 40. Thus, a gas of predetermined pressure can be charged into the interior of the hand piece 13 by connecting the gas generating unit 42 before the treatment. After the charging of the gas, it is brought into a state where the gas is sealed off in a similar manner as the sealed-off vacuum as described above. Since the gaseous atmosphere is provided at the interior of the hand piece 13, the discharge threshold value in the vicinity of the beam converging point F is augmented comparing to the case where air is provided as the atmosphere. The laser discharge at the beam converging point F will be prevented or controlled in a manner similar to that described above, whereby a set amount of treatment energy will be obtained.

Such gas charging means is not limited to the hand piece and it is also possible to charge the gas into the interior space throughout the mirror joint assembly and the hand piece by supplying the gas from a port at the same position as the one shown in FIG. 2. In this manner, even if a beam converging point exists within the mirror joint assembly, the laser discharge at such point may be prevented or controlled at the same time.

Further, such charging of the gas may also be attached to a predetermined position on the mirror joint assembly 12 or to a predetermined position on the laser generator (ruby laser) 10.

Figure 6:
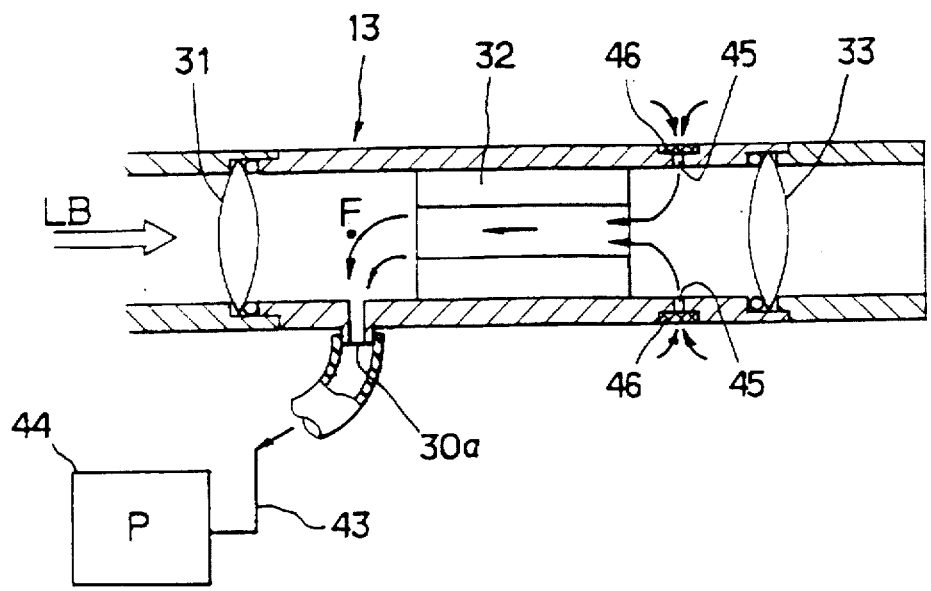
FIG. 6 is an axial sectional view of the hand piece according to a third example.

FIG. 6 shows a further construction of the hand piece 13 according to a third example. The hand piece 13 is constructed such that a fresh air continually flows in and out through the interior thereof. Specifically, an air exhausting pump 44 is connected through a hose 43 to a port 30a which is formed on the cylinder 30 between the light guiding lens 31 and the uniform light irradiation member 32. Further, a sucking port 45 is formed to the cylinder 30 at a position between the uniform light irradiation member 32 and the projecting lens 33, the sucking port 45 being covered with a filter 46.

Here, when the pump 44 is operated, an external air flows into the hand piece 13 through the sucking port 45 and such air is exhausted from the pump 44. For this reason, a fresh air, cleaned by the filter, flows at all times as indicated by arrows in FIG. 6 through the interior space of the hand piece 13 including the beam converging point F. As a result, since a fresh air without being ionized continually enters the position of the beam converging point, the discharge threshold in the interior space including the beam converging point F becomes higher than that in the case where air is simply caused to stay, so that a laser discharge is less likely to occur. That is, it is possible to obtain substantially the same effects and advantages as those of the above described cases of vacuum and gas-sealed states.

Figure 7:
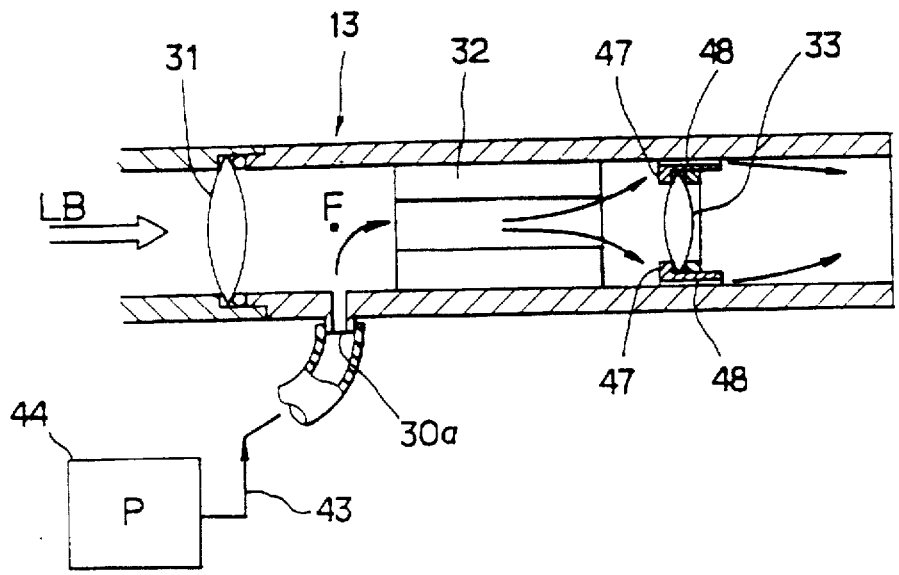
FIG. 7 is an axial sectional view of the hand piece according to a fourth example.

FIG. 7 shows a still further construction of the hand piece according to a fourth example. In this example, although a fresh air is caused to flow at all times through the interior of the hand piece 13, the direction of discharging of the air is different from the construction of FIG. 6. Specifically, a pump 44 capable of supplying a fresh air is connected through a hose 43 to a port 30a which is formed between the light guiding lens 31 and the uniform light irradiation member 32 in the cylinder 30.

Further, air exhausting holes 48, - - - , 48 are formed on a ring-like support member 47 for supporting the projecting lens 33 within the cylinder 30 to communicate the two chambers with each other which are separated by the projecting lens 33.

Here, when the pump 44 is operated, a fresh air is supplied into the hand piece 13 and such air escapes to the treatment surface side through the exhausting holes 48, - - - , 48 formed around the the projecting lens 33. Thereby, an air flow substantially opposite in direction to the one described above occurs at the interior of the hand piece 13 and a fresh air is actively blown to the surface of the projecting lens 33. As a result, a stable medical treatment energy may be obtained, in addition to effecting control over and/or prevention of a laser discharge, since dust or the like on the surface of the projecting lens 33 is also blown to help prevention of stains on the lens.

Figure 8:
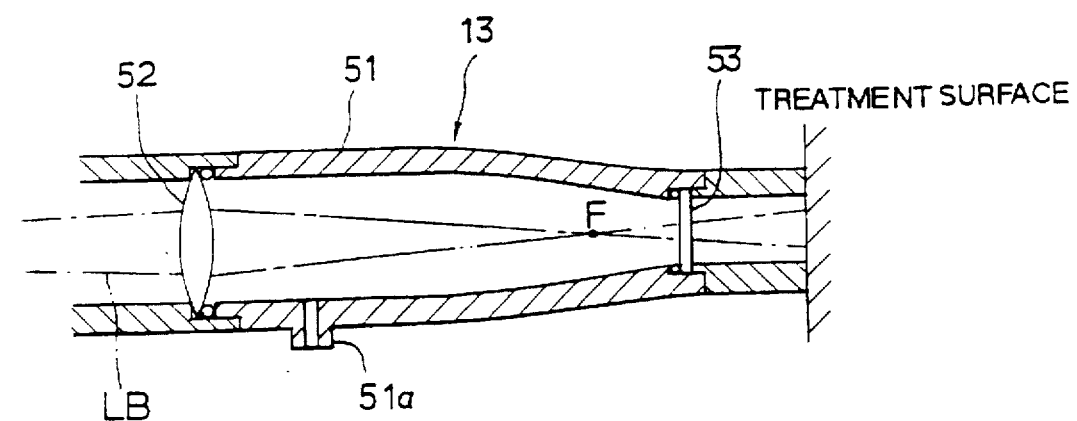
FIG. 8 is an axial sectional view of the hand piece according to a fifth example.
Figure 12:
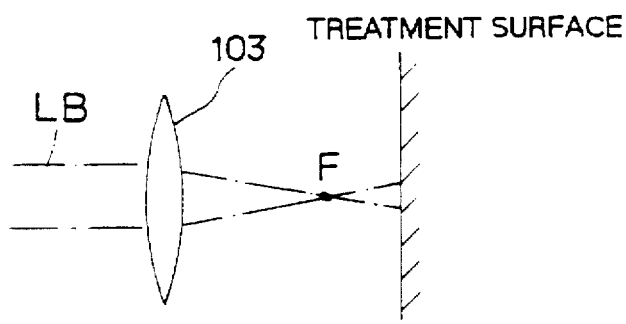
FIG. 12 also shows an optical structure of a hand piece of a lens type according to another conventional example.

FIG. 8 shows a still further construction of the hand piece 13 according to a fifth example. This hand piece 13 corresponds to the one shown in FIG. 12 illustrating a conventional example. That is, this is a hand piece of the lens type. Specifically, a projecting lens 52 is disposed in an air-tight manner with respect to a cylindrical body (cylinder) 51 on the mirror joint side of the cylinder 51, and a light transmitting plate 53 such as of a quartz glass plate is disposed in an air-tight manner with respect to the cylinder 51 at a position toward the treatment surface side separated by a predetermined distance from the lens 52. A port 51a is provided on the cylinder 51 between the lens 52 and the light transmitting plate 53. The vacuum pump or gas generation unit of the type described above is connected to the port 51a. The fact that the light transmitting plate 53 is additionally provided also helps prevention of stains on the projecting lens 52.

By making the light transmitting plate 53 as replaceable, stable treatment energy can be obtained, which is less expensive than replacing of the lens.

In this manner, even with the hand piece 13 of the lens type, it is possible to produce a vacuum at or to charge a gas into the interior thereof and a sealed-off vacuum or a sealed-off gas are also made possible. As a result, in a manner similar to that in the foregoing examples, the laser discharge at the beam converging point F may be controlled or prevented to obtain a medical treatment energy that is sufficient and stable.

Further, with this hand piece of lens type, it is not necessary to use a lens with a relatively long focal length to set the treatment surface of a human body, for example, toward the lens side of the light converging position. For this reason, even if it is erroneously emitted into the air, the energy density of the laser beam at the irradiation surface is smaller comparing with the case of using such long-focus lens. Thus, the arrangement of only the protective glasses provides sufficient measures for the protection of patients and physicians.

Of course, the method of augmenting the discharge threshold value by a gas flow as shown in FIGS. 6 and 7 may also be applied to the hand piece of lens type.

Furthermore, the laser generator serving as the laser beam generation means in the above embodiments is not limited to a ruby laser, and it may be of other lasers of a wavelength according to the characteristic of the location of treatment. Moreover, the light guiding means is not limited to the above described mirror joint assembly and it suffices to be able to guide a laser beam of giant pulse. For example, it may also be a hollow fiber made of glass or a hollow metal light guiding path.

Figure 9:
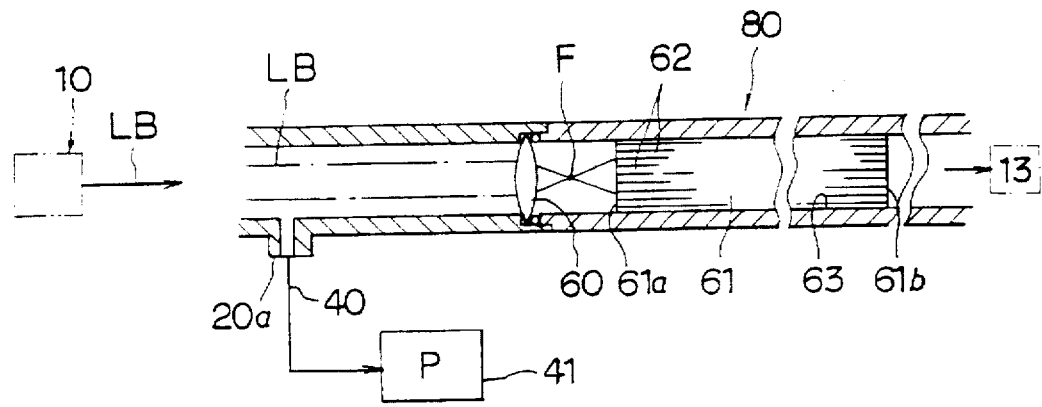
FIG. 9 shows an axial sectional view of a further embodiment of the present invention in which an optical fiber means is utilized.

As shown in FIG. 3, the light guiding lens 31 is FIG. 9 represents a further embodiment of the present invention showing a case in which the air stay preventing means is provided for a light guiding means 80, connecting the laser beam generation means 10 and the hand piece 13, at a portion on the side of the laser beam generation means 10. FIG. 9 shows one example of this embodiment which is applied to the example of FIG. 2 in which the vacuum means is provided for the mirror joint assembly 12, but in this example, the vacuum means is provided for the light guiding means 80. That is, in this example, the mirror joint assembly 12 including a plurality of mirrors is substituted with the cylindrical light guiding means 80 of simple structure.

With reference to FIG. 9, an optical fiber means 61 is disposed in the light guiding means 80 in place of the hand piece 13. The optical fiber means 61 comprises an outer cylindrical clad or sheath 63 disposed inside the cylindrical light guide means 80 coaxially therewith and a number of fine optical fibers 62 extending straightly from an input side end 61a of the clad 63 to an output side end 61b thereof, the optical fibers 62 being bundled.

The use of the optical fiber eliminates complicated light guide adjustment by using such as mirrors, thus improving the maneuverability of the apparatus, resulting in reducing of production cost.

In general, however, it is difficult for an optical fiber to guide a light at an energy density of about 101 MW/mm$^2$, breakage threshold value, because of breaking thereof, and accordingly, it is difficult to effectively use single optical fiber having a large diameter. In addition, the single optical fiber having a large diameter has no good flexible property, thus being not suitable for use.

In this embodiment, because of the above reason, a number of fibers 62, being bundled, are utilized to make less the breakage threshold value per single fiber than the above value, whereby it becomes possible to guide the laser beam of high power.

It is preferred that the optical fibers 62 are fused or resin-bonded at the laser beam input and output side ends for forming the bundle and intermediate portions thereof are not fused or bonded for maintaining their flexibility.

In a preferred example, quartz glass fibers may be utilized for the optical fibers of this embodiment.

According to this embodiment, the beam converging point F is formed between the light guiding leans 60 and the optical fiber means 61, and the laser discharge at the light converging point F can be surely prevented or controlled. The laser beam energy reaching the treatment skin surface is hardly reduced so that a predetermined energy necessary for the treatment is secured and the treating energy is made stable. As a result, lack of energy can be eliminated through the bundle of fine optical fibers and the deep birthmark or the like can be well treated by means of a giant pulse.

Figure 10:
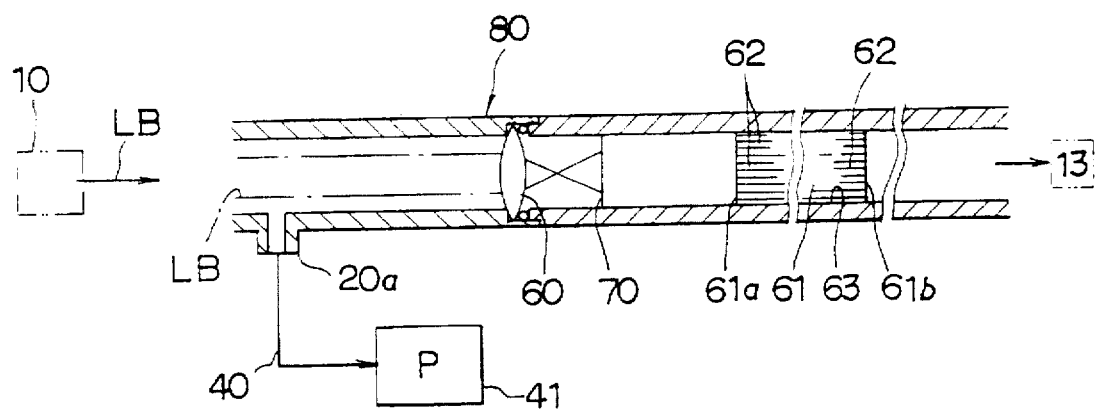
FIG. 10 also shows an axial sectional view of a still further embodiment of the present invention in which a laser beam uniform irradiation means is further provided in connection with the optical fiber means of FIG. 9.
Figure 11:
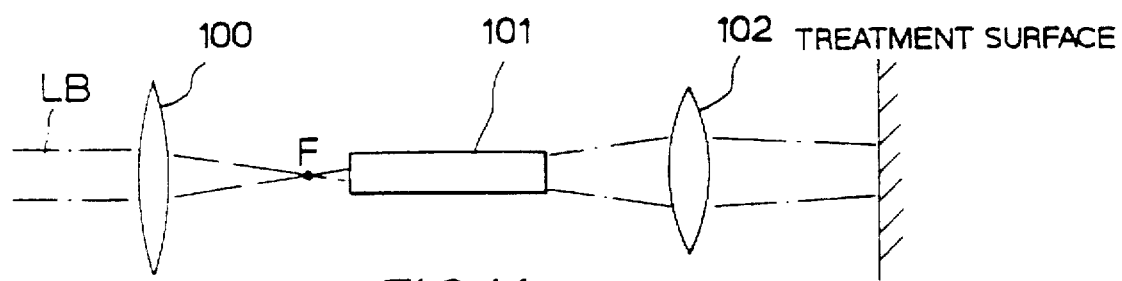
FIG. 11 is an illustration of an optical structure of arrangement of a hand piece according to a conventional example.

FIG. 10 represents a modified embodiment of FIG. 9, in which a uniform light irradiation member, preferably a KALEIDSCOPE commercially known, 70 is disposed between the light guiding lens 60 and the optical fiber means 61. The light output side end of the uniform light irradiation member 70 is connected to the input side end of the optical fiber means 61. The arrangement of the uniform light irradiation member 70 makes it possible to uniformly distribute the laser beam energy to be guided into the optical fiber means 61 in the view point of the uniform energy density at the input side end of the optical fiber means 61. According to this embodiment, this characteristic feature can be obtained in addition to the advantages of the embodiment of FIG. 9. The uniform light irradiation member 70 may have a structure substantially similar to that 32 of the former embodiment.

The embodiments of FIGS. 9 and 10 utilizing the optical fiber means are shown in combination of the vacuum means 40 and 41 for creating the vacuum state in the light guide means 80 disposed in front of the light guiding lens 60 as shown in FIG. 2, but the examples of FIGS. 4 to 8 for creating the vacuum state, gas sealing state and air flowing stage may be combined with no problem with the embodiments of FIGS. 9 and 10.

For example, as shown in FIG. 4, the vacuuming port 20a will be formed at a position on the cylindrical light guide means 80 on the side of the laser beam generation means. The vacuuming port 20a is connected to a vacuum pump 41 through a hose 40. The hose 40 is extended to trail the outer surface of the light guide means 80. The structure shown in FIG. 3 may be also applicable to these embodiments of FIGS. 9 and 10.

As has been described above, according to the present invention, there is provided a laser medical treatment apparatus comprising a laser beam generation means for outputting a laser beam of giant pulse, a light guiding means for guiding the laser beam outputted from the laser beam generation means, and a hand piece attached to a terminal end of the light guiding means and irradiating the laser beam on a location of a birthmark to be treated. According to this arrangement, a beam converging point is provided within the laser beam propagating path in at least one of the light guiding means and the hand piece. A predetermined region in the laser beam propagating path including at least the beam converging point is brought into one of a vacuum state, a gas sealed state and a state in which air is continually caused to flow, so that a condition in which air stays still in the predetermined region is prevented. For this reason, a discharge threshold value in the predetermined region is significantly augmented comparing with the case where air stays still. Since laser discharge at the beam converging point is surely prevented or controlled, the energy of the laser beam is hardly vanished.

As described hereinbefore, according to the present invention, a deep birthmark or the like of a human body may be well treated, since it is possible to obtain an energy for medical treatment at an expected and stable level. Further, in the case of using a lens-type hand piece, it is not necessary in order to avoid a laser discharge to unreasonably set the treatment surface between the lens and the light converging point. Protective glasses thus provide sufficient safety measures against erroneous emission.

It is also to be noted that the present invention is described hereinbefore through preferred embodiments, but it is not limited to the described embodiments and many other changes and modification including combination of embodiments may be done according to the principle of the present invention without departing from the scope of the appended claims.

What is claimed is:

1. A laser apparatus for medical treatment use in which a laser beam is irradiated on a portion of a human body to be treated, comprising:

means for generating a laser beam of giant pulse;

a light guide means having one end through which the laser beam outputted from the laser beam generation means is guided;

a hand piece attached to another end of the light guide means for propagating the laser beam from the light guide means so as to irradiate the laser beam propagated in the hand piece to the portion to be treated;

means for forming a beam converging point within at least a laser beam propagating path located in the hand piece; and means for keeping a gas at predetermined pressure in at least a predetermined region in the laser beam propagating path, said predetermined region including the beam converging point and said gas maintained at said predetermined pressure preventing a laser discharge at the beam converging point.

2. A laser medical treatment apparatus according to claim 1, wherein said gas keeping means is communicated with the predetermined region.

3. A laser medical treatment apparatus according to claim 2, wherein said gas keeping means is connected to the hand piece.

4. A laser medical treatment apparatus according to claim 3, wherein said gas keeping means has a gas charging unit for charging the gas at least into an interior of the hand piece at least before the medical treatment and has a sealing unit communicated with at least the laser beam propagating path and the gas charging unit for sealing the charged gas at least in the laser beam propagating path during the medical treatment.

5. A laser medical treatment apparatus according to claim 4, wherein said sealing unit has a port communicated with the predetermined region of the hand piece and the gas charging unit and has a sealing member attached to the port for opening and shutting the port, said port being opened by the sealing member while charging the gas into the interior of the hand piece and being shut thereby after the gas is charged fully in the interior of the hand piece.

6. A laser medical treatment apparatus according to claim 5, wherein said gas charging unit is removed from the port after the port is shut by the sealing member.

7. A laser medical treatment apparatus according to claim 4, wherein said gas is one of He and Ne.

8. A laser medical treatment apparatus according to claim 1, wherein said beam converging point forming means comprises a light guiding lens disposed in the hand piece for narrowing the laser beam having been propagated by the light guide means to form the beam converging point.

9. A laser medical treatment apparatus according to claim 8, wherein said hand piece includes a cylindrical body portion, further comprising:

a uniform light irradiation member disposed in said cylindrical body portion between the portion to be treated and the beam converging point so as to output a uniform laser beam on the basis of a laser beam having been transmitted through the light guiding lens.

10. A laser medical treatment apparatus according to claim 9, wherein said uniform light irradiation member includes a cavity, further comprising a projecting lens disposed in said cylindrical body portion on an output side of the uniform light irradiation member so as to irradiate the uniform laser beam onto the portion of the human body to be treated.

11. A laser medical treatment apparatus according to claim 8, wherein said light guide means comprises a mirror joint assembly.

12. A laser medical treatment apparatus according to claim 1, wherein said beam converging point forming means comprises a lens disposed in the hand piece for narrowing the laser beam having been propagated by the light guide means to form the beam converging point and said handpiece has a cylindrical body portion, said cylindrical body portion being provided with a light transmitting member disposed between the beam converging point and the portion to be treated so as to irradiate a laser beam after having been transmitted through the lens onto the portion of the human body to be treated.

* * * * *